US00PP19482P2

(12) United States Plant Patent
Klemm

(10) Patent No.: US PP19,482 P2
(45) Date of Patent: Nov. 25, 2008

(54) ***ANGELONIA* PLANT NAMED 'KLEAA06550'**

(50) Latin Name: *Angelonia augustifolia*
Varietal Denomination: KLEAA06550

(75) Inventor: Nils Klemm, Stuttgart (DE)

(73) Assignee: Klemm + Sohn GmbH + Co KG, Stuttgart (DE)

( * ) Notice: Subject to any disclaimer, the term of this patent is extended or adjusted under 35 U.S.C. 154(b) by 0 days.

(21) Appl. No.: 12/002,473

(22) Filed: Dec. 17, 2007

(51) Int. Cl.
*A01H 5/00* (2006.01)

(52) U.S. Cl. ..... Plt./404

(58) Field of Classification Search ..... Plt./404
See application file for complete search history.

(56) References Cited

PUBLICATIONS

UPOV ROM GTITM Computer Database, GTI Jouve Retreival Software May 2007 Citation for 'KLEAA06550'.*

* cited by examiner

*Primary Examiner*—Wendy C. Haas
(74) *Attorney, Agent, or Firm*—C. A. Whealy

(57) ABSTRACT

A new and distinct cultivar of *Angelonia* plant named 'KLEAA06550', characterized by its upright and compact plant habit; freely branching habit; freely flowering habit; violet-colored flowers with white-colored centers; and good garden performance.

1 Drawing Sheet

Botanical designation: *Angelonia augustifolia.*
Cultivar denomination: 'KLEAA06550'.

BACKGROUND OF THE INVENTION

The present invention relates to a new and distinct cultivar of *Angelonia,* botanically known as *Angelonia augustifolia* and hereinafter referred to by the name 'KLEAA06550'.

The new *Angelonia* is a product of a planned breeding program conducted by the Inventor in Stuttgart, Germany. The objective of the breeding program is to create new compact *Angelonia* cultivars that are freely branching, flower early and have unique flower coloration.

The new *Angelonia* originated from a cross-pollination made by the Inventor in 2003 in Stuttgart, Germany of a proprietary selection of *Angelonia augustifolia* identified as code number A 003, not patented, as the female, or seed, parent and a proprietary selection of *Angelonia augustifolia* identified as code number A 002, not patented, as the male, or pollen, parent. The new *Angelonia* was discovered and selected by the Inventor as a single flowering plant within the progeny of the stated cross-pollination in a controlled environment in Stuttgart, Germany in April, 2004.

Asexual reproduction of the new *Angelonia* by cuttings in a controlled environment in Stuttgart, Germany since May, 2004, has shown that the unique features of this new *Angelonia* are stable and reproduced true to type in successive generations.

SUMMARY OF THE INVENTION

The cultivar KLEAA06550 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'KLEAA06550'. These characteristics in combination distinguish 'KLEAA06550' as a new and distinct cultivar of *Angelonia:*

1. Upright and compact plant habit.
2. Freely branching habit.
3. Freely flowering habit.
4. Violet-colored flowers with white-colored centers.
5. Good garden performance.

Plants of the new *Angelonia* differ from plants of the parent selections primarily in flower color.

Plants of the new *Angelonia* can be compared to plants of the cultivar Angelina Dark Blue, not patented. Plants of the new *Angelonia* and the cultivar. Angelina Dark Blue differ in the following characteristics:

1. Plants of the new *Angelonia* are not as compact as and more upright than plants of the cultivar Angelina Dark Blue.
2. Plants of the new *Angelonia* are and the cultivar Angelina Dark Blue differ in flower color as plants of the cultivar Angelina Dark Blue do not have white-colored centers.

BRIEF DESCRIPTION OF THE PHOTOGRAPH

The accompanying colored photograph illustrates the overall appearance of the new *Angelonia,* showing the colors as true as it is reasonably possible to obtain in colored reproductions of this type. Colors in the photograph may differ slightly from the color values cited in the detailed botanical description which accurately describe the colors of the new *Angelonia.* The photograph comprises a side perspective view of a typical flowering stem of 'KLEAA06550'.

DETAILED BOTANICAL DESCRIPTION

The aforementioned photograph and following observations, measurements and values describe plants grown in Stuttgart, Germany during the spring and summer under commercial practice in an outdoor nursery with day temperatures ranging from 15° C. to 35° C., night temperatures ranging from 12° C., to 20° C. Plants were pinched once about four weeks after planting. Plants had been growing for about four months when the photograph and description were taken. In the following description, color references are made to The Royal Horticultural Society Colour Chart, 1995 Edition, except where general terms of ordinary dictionary significance are used.

Botanical classification: *Angelonia augustifolia* cultivar KLEAA06550.

Parentage:

*Female, or seed, parent.*—Proprietary selection of *Angelonia augustifolia* identified as code number A 003, not patented.

*Male, or pollen, parent.*—Proprietary selection of *Angelonia augustifolia* identified as code number A 002, not patented.

Propagation:

*Type.*—By cuttings.

*Time to produce a rooted young plant, summer.*—About 25 days at 25° C.

*Time to produce a rooted young plant, winter.*—About 32 days at 20° C.

*Root description.*—Fine, fibrous; white in color.

Plant description:

*Plant form/habit.*—Herbaceous perennial. Upright and compact plant habit. Freely branching habit; when pinched, lateral branches form at the nodes. Moderately vigorous growth habit.

*Plant height.*—About 25 cm.

*Plant width (spread).*—About 30 cm.

*Lateral branches.*—Length: About 7 cm. Diameter: About 1 mm. Internode length: About 1 cm to 3 cm. Strength: Moderately strong. Texture: Smooth, glabrous. Color, upper surface: 200B. Color, lower surface: 142A.

Foliage description:

*Arrangement.*—Opposite; simple; sessile.

*Length.*—About 1 cm to 6 cm.

*Width.*—About 0.5 cm to 1.5 cm.

*Shape.*—Oblong.

*Apex.*—Acute.

*Base.*—Obtuse.

*Margin.*—Crenate.

*Texture, upper and lower surfaces.*—Smooth, glabrous.

*Venation pattern.*—Pinnate.

*Color.*—Developing leaves, upper and lower surfaces: 143B. Fully expanded leaves, upper surface: 137A; venation, 137A. Fully expanded leaves, lower surface: 137C; venation, 137A.

Flower description:

*Flower type/habit.*—Single flowers arranged in terminal racemes; flowers face mostly outward. Freely flowering habit; about 65 to 80 flowers develop per lateral stem.

*Fragrance.*—None detected.

*Natural flowering season.*—Continuously flowering from spring through summer in Germany. Plants begin flowering about eleven weeks after planting. Flowers not persistent.

*Postproduction longevity.*—Flowers last about five to ten days on the plant.

*Flower buds.*—Height: About 2 mm to 5 mm. Diameter: About 2 mm to 5 mm. Shape: Ovate. Color: Upper surface, 149B; lower surface, 141C.

*Inflorescence height.*—About 4 cm to 6 cm.

*Inflorescence diameter.*—About 3 cm.

*Flower diameter.*—About 1.5 cm.

*Flower depth.*—About 5 mm.

*Petals.*—Quantity per flower: Typically five in a single whorl; petals fused at the base. Length: About 6 mm. Width: About 6 mm. Shape: Roughly spatulate. Apex: Obtuse. Margin: Entire. Texture, upper and lower surfaces: Smooth, glabrous; velvety. Color: When opening, upper and lower surfaces: 82B; color becoming closer to 86C with development; lower petal with a white, close to 155D, spot towards the base. Fully opened, upper and lower surfaces: 86C.

*Sepals.*—Quantity per flower: Typically five in a single whorl. Length: About 3 mm to 4 mm. Width: About 1 mm to 2 mm. Shape: Ovate. Apex: Acute. Base: Obtuse. Margin: Entire. Texture, upper and lower surfaces: Smooth, glabrous. Color, upper surface: 183A. Color, lower surface: 143B.

*Pedicels.*—Length: About 1 cm. Diameter: About 0.3 mm. Angle: About 100° to 120° from vertical. Strength: Moderately strong; flexible. Texture: Smooth, glabrous. Color: 183A.

*Reproductive organs.*—Stamens: Quantity per flower: Typically four. Anther shape: Ovate. Anther length: About 1 mm. Anther color: 85B. Pollen amount: Moderate. Pollen color: 155A. Pistils: Quantity per flower: One. Pistil length: About 2 mm. Stigma shape: Filamentous. Stigma color: 155D. Style color: 155D. Ovary color: 155D.

*Seeds/fruits.*—Seed and fruit development have not been observed.

Disease/pest resistance: Plants of the new *Angelonia* have not been noted to be resistant to pathogens and pests common to *Angelonia*.

Garden performance: Plants of the new *Angelonia* have been observed to have good garden performance and tolerate rain, wind and temperatures ranging from about 10° C. to 40° C.

It is claimed:

1. A new and distinct *Angelonia* plant named 'KLEAA06550' as illustrated and described.

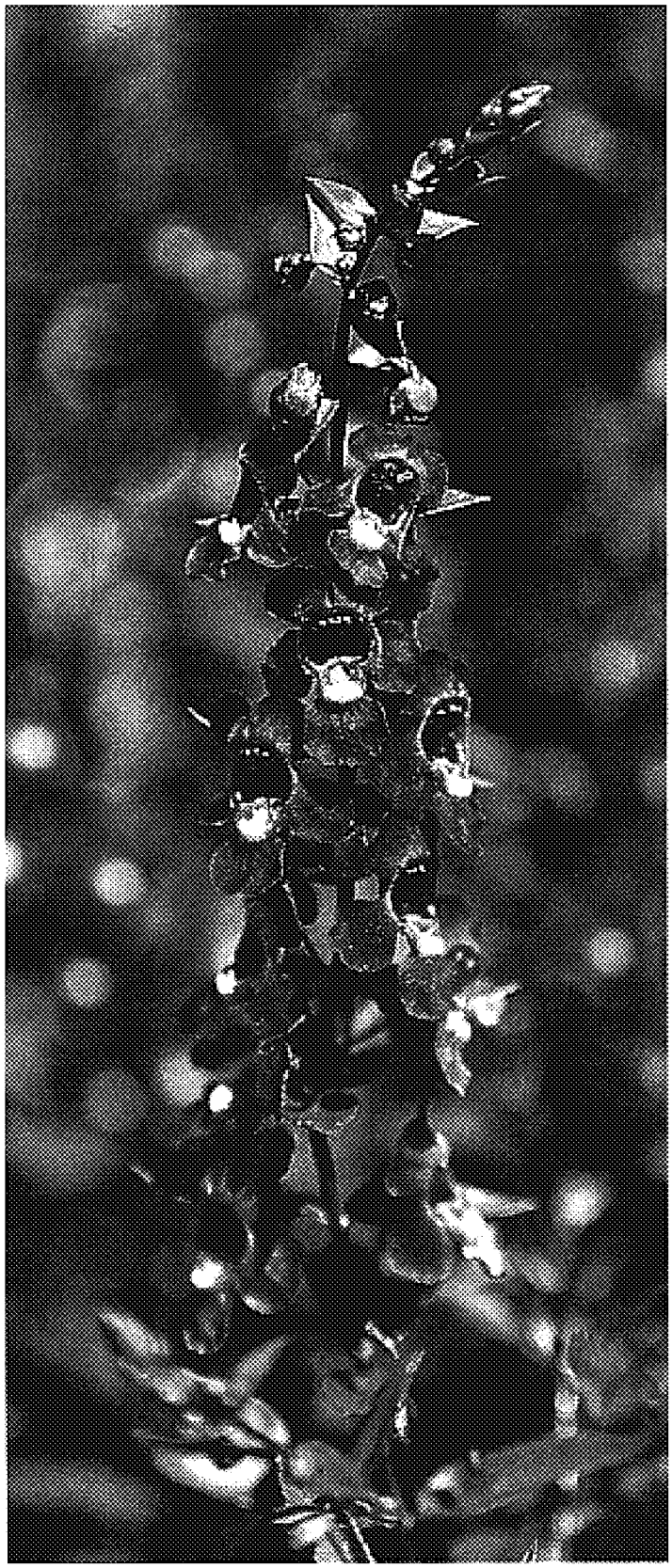

* * * * *